United States Patent
Hiratsuka et al.

(10) Patent No.: US 7,982,472 B2
(45) Date of Patent: *Jul. 19, 2011

(54) RESISTANCE MEASUREMENT METHOD AND COMPONENT INSPECTION PROCESS

(75) Inventors: Yoshiaki Hiratsuka, Kawasaki (JP); Akio Ikeda, Kawasaki (JP); Masaharu Suzuki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 63 days.

This patent is subject to a terminal disclaimer.

(21) Appl. No.: 12/153,528

(22) Filed: May 20, 2008

(65) Prior Publication Data
US 2009/0033344 A1 Feb. 5, 2009

(30) Foreign Application Priority Data
Jul. 31, 2007 (JP) ................................. 2007-199465

(51) Int. Cl.
*G01R 27/08* (2006.01)

(52) U.S. Cl. .......................... 324/693; 324/722; 324/724

(58) Field of Classification Search .................. 324/600, 324/693, 722, 724
See application file for complete search history.

(56) References Cited

U.S. PATENT DOCUMENTS
| 3,818,279 | A | * | 6/1974 | Seeger et al. ................. 361/751 |
| 4,861,453 | A | * | 8/1989 | Matsuoka et al. ............ 204/404 |
| 6,478,909 | B1 | * | 11/2002 | Tuttle .............................. 156/85 |
| 2008/0180115 | A1 | | 7/2008 | Hiratsuka et al. |

FOREIGN PATENT DOCUMENTS
| JP | 56-79262 | | 6/1981 |
| JP | 57-154069 | * | 9/1982 |
| KR | 10-2008-0049609 | | 6/2008 |

OTHER PUBLICATIONS

Chinese Office Action issued Jun. 7, 2010 in corresponding Chinese Patent Application 200810109911.2.
Chinese Office Action issued Nov. 19, 2010 in corresponding Chinese Patent Application 200810109911.2.

* cited by examiner

*Primary Examiner* — Timothy J Dole
(74) *Attorney, Agent, or Firm* — Staas & Halsey LLP (57) ABSTRACT

In a first step, two conductive plates such as two zinc galvanized (electroplated) steel plates with films formed on surfaces thereof, are prepared; a flexible conductive material is held between these two zinc galvanized (electroplated) steel plates. A spacer is also held between the two zinc galvanized (electroplated) steel plates to regulate the space therebetween and a measurement object such as a conductive cloth is held between the flexible conductive material and at least one of the zinc galvanized (electroplated) steel plates. In a second step, the electric resistance between the two zinc galvanized (electroplated) steel plates is measured while the flexible conductive material is held together with the measurement object between the two conductive plates.

6 Claims, 8 Drawing Sheets

R1a, R1b } RESISTANCE OF STEEL PLATE

R1a1, R1b1 } RESISTANCE OF FILM

R10: RESISTANCE OF FLEXIBLE CONDUCTIVE MATERIAL
R2a: RESISTANCE OF MEASUREMENT OBJECT

RESISTANCE MEASUREMENT METHOD AND COMPONENT INSPECTION PROCESS

BACKGROUND OF THE INVENTION

1. Field of the Invention

The present invention relates to a resistance measurement method for measuring the electric resistance of a measurement object with a film formed on a surface thereof and a component inspection process to which the resistance measurement method is applied.

2. Description of the Related Art

Metal plate materials have been conventionally used as a material of cabinets for personal computers and racks for housing the personal computers. Such metal plate materials are inexpensive and easily available while providing certain strengths.

Figure 1:
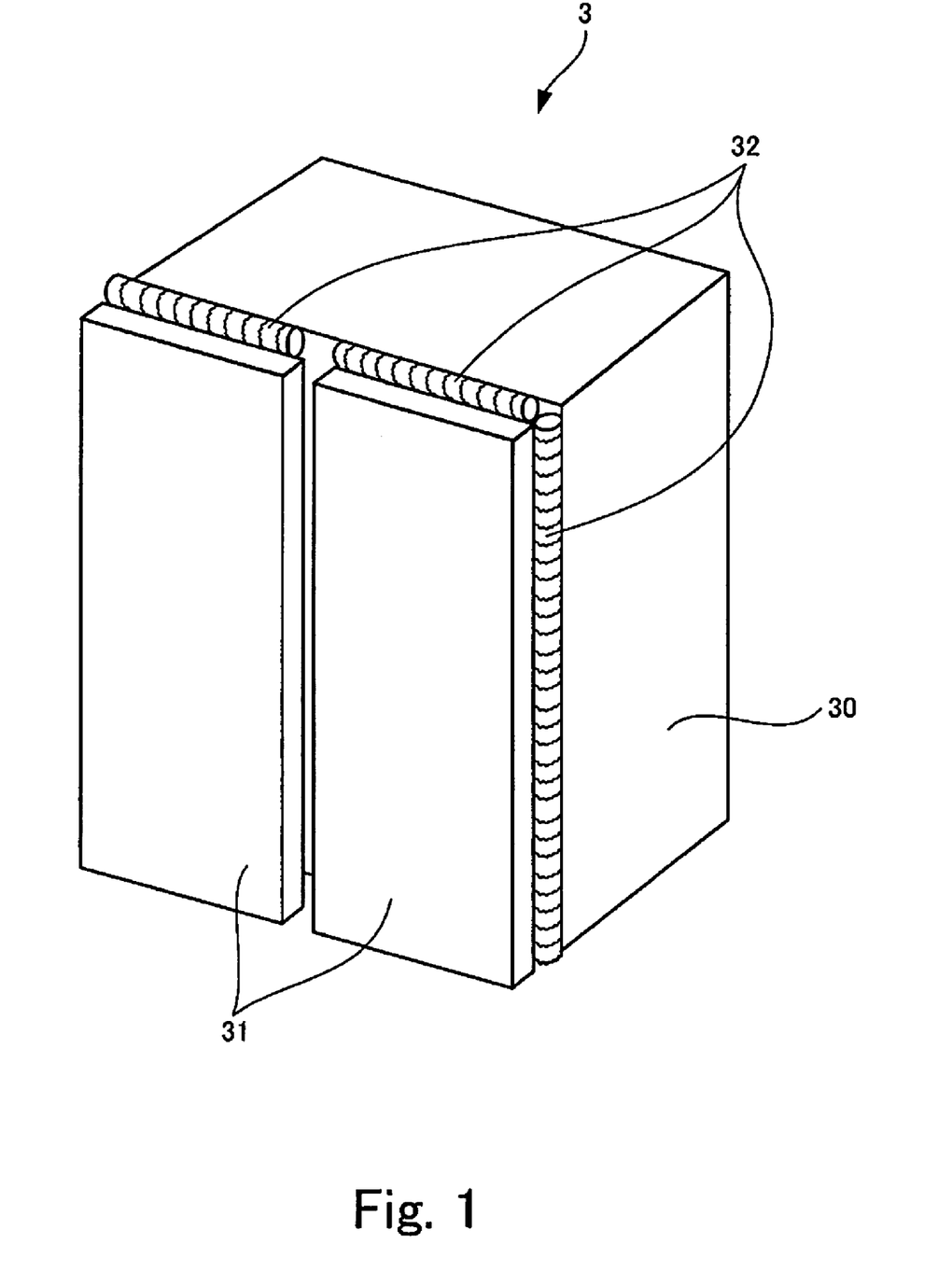
FIG. 1 is a view showing an external appearance of a rack which houses an information processing unit such as a personal computer.

FIG. 1 is a view showing an external appearance of a rack in which an information processing unit such as a personal computer is housed.

Metal plates are used for a rack 3, a housing section 30 and a door section 31 shown in FIG. 1. When the metal plates are used for the rack 3, the housing section 30 and the door section 31 as in this case, the metal plates also serve as shield members to prevent unwanted radiation leak from the personal computer housed in the rack 3 to the outside.

However, the rack 3 tends to have a gap between the door and a section for rotatably supporting the door, or between the door and other sections. When there is unwanted radiation from the personal computer in the rack with such a gap, the radiation leaks to the outside of the personal computer through the gap. Thus, an unwanted radiation prevention member 32 made of a sheet-like conductive rubber, a conductive cloth or the like is provided in the gap to produce a better shield effect. In other words, a member such as the unwanted radiation prevention member 32 also serves as a shield member.

Recent personal computers tend to increasingly cause unwanted radiation at high frequency due to use of high frequency clocks for determining operation speeds. For this reason, in order to improve a shielding function, metal plate materials (or, organic materials having electric conductivity may possibly be used when the organic materials are less expensive) is used for a personal computer cabinet and for the housing section 30 and the door section 31 of the rack shown in FIG. 1.

When the cabinet of a personal computer, the rack, and the like are designed to have a shielding function, it is necessary to evaluate, in advance, the shielding performances of materials for cabinets and racks, such as a metal plate material, a conductive cloth and the like.

In the general evaluation of the shielding performance of a metal plate material, the electric resistance of the metal plate material is measured using a resistance measurement method in accordance with the specification of JIS-C-2550, and then the evaluation is made according to the principle that the lower the measured electric resistance, the higher the shielding performance. Currently, general-purpose galvanized steel plates or the like, which are easily available as described above, are used as plate materials for fabricating cabinets and racks for personal computers. The galvanized steel plates are surface-treated (anti-corrosive treated or the like) in a way different depending on a manufacturer. In some cases, the conditions of surface treatment may differ even by the single manufacturer. Therefore, when the evaluation is performed, the electric resistance of a plate including the surface treatment must be measured first, and then the characteristics including the surface treatment must be evaluated for the plate.

However, when the electric resistance of a metal plate material is measured by using the resistance measurement method in accordance with the specification of JIS-C-2550, a sharp probe breaks a film formed on the surface of plate, resulting in that the electric resistance of the steel plate under the film is measured. Consequently, the same values of the electric resistance are measured even though the steel plates have different surface treatments.

Hence, to solve this problem, a technique is proposed in Japanese Patent Application Publication No. Sho 57-154069, in which a conductive rubber is used to measure the electric resistance without breaking a film on the surface. The conductive rubber used in Japanese Patent Application Publication No. Sho 57-154069 is a conductive material having almost the same characteristics as metal. The conductive rubber is used as a material preventing unwanted radiation by filling a gap between the housing section and the door section as shown in FIG. 1. The conductive rubber is also used as a member to easily connect a land pattern and a terminal of a leadless part on a substrate as proposed in Japanese Patent 4 Application Publication No. Sho 56-79262. The technique described in Japanese Patent Application Publication No. Sho 57-154069 enables the performance evaluation of each of plate materials manufactured by different manufacturers, and also enables the performance evaluation of each of multiple plate materials manufactured by a single manufacturer. Accordingly, plate materials suitable for the fabrication of cabinets and racks can be appropriately selected.

Although the technique of Japanese Patent Application Publication No. Sho 57-154069 enables measurement of a resistance value of a plate material, it is difficult to apply the technique to measurement and evaluation of materials such as a conductive rubber and a conductive cloth because these materials tend to deform easily. In the case of the rubber or the conductive cloth, difficulty in maintaining its shape makes it difficult to obtain stable measured values. Therefore, a technique enabling accurate and stable measurement of resistance value has been desired. Further, in some cases, paints are applied to some procured plate materials before or after the plate materials are assembled into cabinets and racks. In such a case, since a film formed by the application of the paint affects the shielding characteristics of the cabinets and the like, a technique enabling accurate and stable measurements of resistance values has also been desired for the rubber and the cloth.

SUMMARY OF THE INVENTION

The present invention has been made in view of the above circumstances and provides a resistance measurement method for an accurate and stable measurement of the electric resistance of a sheet-like, a cloth-like, or a film-like measurement object. The present invention also provides a component inspection process to which the resistance measurement method is applied.

A resistance measurement method according to an aspect of the present invention includes:

a first step of holding a flexible conductive material between two conductive plates, and interposing a measurement object between at least one of the two conductive plates and the flexible conductive material; and a second step of measuring electric resistance between the two conductive plates that hold the flexible conductive material therebetween with the measurement object interposed.

According to the resistance measurement method of the present invention, a conductive material held between the two conductive plates is compressed by pressures applied from the both sides of the two conductive plates held between the two conductive plates so that the flexible conductive material comes into and stays in contact with a measurement object. Thereafter, the electric resistance between the two conductive plates is measured in the second step. Thus, even though the measurement object is a sheet-like, a cloth-like, or a film-like object, the measurement object comes to a stable state in which the measurement object is pressed onto the conductive plate by a flexible conductive material (for example, a conductive rubber, a material around which a conductive cloth is wrapped, a conductive spring, or the like, which is hereinafter referred to as a flexible conductive material). In addition, contact resistance between a probe and the conductive plate is caused to be in a state in which the contact resistance is approximately zero, so that the resistance of the measurement object can be accurately measured. In other words, when the electric resistance of the measurement object is measured using the resistance measurement method of the present invention, the electric resistance of the measurement object can be accurately measured even though the measurement object is a sheet-like, a cloth-like, or a film-like object.

Here, when accurate measurement of a measurement object becomes possible by using the resistance measurement method of the present invention, for example, the electric resistance of each one of measurement objects manufactured by multiple manufacturers is measured and the respective measurement results are compared to evaluate the manufacturers. Further, the electric resistance of each one of a number of measurement objects manufactured by a same manufacturer is measured and the respective measurement results are compared to evaluate a number of respective measurement objects.

Preferably, the first step may be a step of holding a spacer as well as the flexible conductive material between the two conductive plates, the spacer regulating a space between the two conductive plates.

When pressures are applied to the flexible conductive material from the both sides of the two conductive plates while the flexible conductive material is being held between the two conductive plates and the flexible conductive material is compressed, it is likely that the resistance value of the flexible conductive material changes to some degree according to the change of the magnitude of the compression. Thus, when the space between the two conductive plates is regulated by the spacer, the measurement accuracy improves because the compression to the flexible conductive material remains constant.

It is also preferable, in the resistance measurement method of the present invention, to include a third step of holding the flexible conductive material between the two conductive plates in the same state as the first step but without interposing the measurement object between the two conductive plates; and a fourth step of measuring electric resistance between the two conductive plates that hold the flexible conductive material therebetween without interposing the measurement object, wherein the third and fourth steps are performed before or after the first and second steps.

In steps 3 and 4, a reference resistance value excluding that of the measurement object is obtained while the resistance value including that of the measurement object is obtained in steps 1 and 2. A difference between these resistance values is then obtained, so that the resistance value of the measurement object alone is accurately obtained.

Further, the electric resistance value of the flexible conductive material may be known.

A flexible conductive material has shown a certain amount of resistance. For that reason, after obtaining a measurement result, the electric resistance of the flexible conductive material is subtracted from the result, so that the electric resistance of the measurement object can be accurately measured.

Incidentally, it should be noted that the conductive plate may be made of any one of a zinc galvanized steel plate, a zinc electroplated steel plate, a stainless steel plate, a steel plate, a copper plate, an alloy material, aluminum and a resin, or may have a film formed thereon.

Further, the spacer may be thinner than the flexible conductive material which is in an uncompressed state, or may be an insulating material.

Thus, the space between the two conductive plates is regulated by the spacer which is made of an insulating material, and the thickness of which is smaller than that of the flexible conductive material being in an uncompressed state. Accordingly, a highly reproducible measurement of the measurement object being stable in a compressed state can be made.

A component inspection process according to another aspect of the present invention measures the electric resistance of an inspection object to determine whether the inspected object is acceptable according to the measurement result, and the process includes:

a first step of holding a flexible conductive material between two conductive plates, and interposing an inspection object between at least one of the two conductive plates and the flexible conductive material; and a second step of measuring electric resistance between the two conductive plates that hold the flexible conductive material therebetween with the measurement object interposed.

Since the resistance measurement method of the present invention is applied to the component inspection process of the present invention, it is possible to accurately determine the shielding performance of the conductive cloth by measuring the electric resistance of, for example, the conductive cloth as an inspection object.

Note that, only a basic configuration of the component inspection process of the present invention is shown here to avoid redundancy. The component inspection process of the present invention includes not only the above basic configuration, but also various configurations corresponding to respective configurations of the resistance measurement methods described above.

As described above, according to the present invention, an accurate and stable measurement of the electric resistance of a sheet-like, a cloth-like, or a film-like measurement object can be made.

DETAILED DESCRIPTION OF THE INVENTION

Embodiments of the present invention will be described below with reference to the accompanying drawings.

Figure 2:
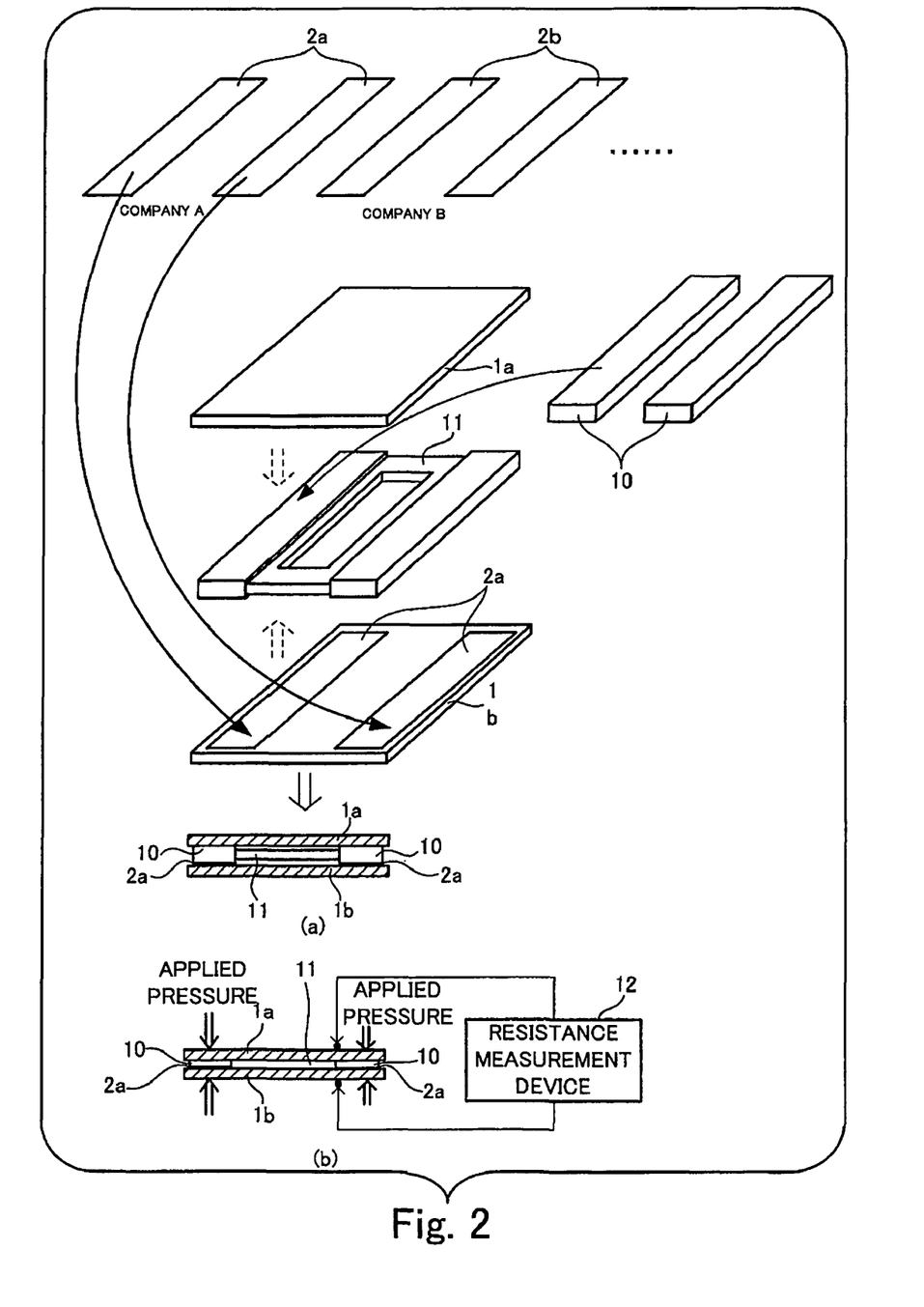
FIG. 2 is an explanatory view explaining a resistance measurement method by which the resistance of an unwanted radiation prevention member is measured, the member being provided in a gap between a housing section and a door section of the rack shown in FIG. 1.

FIG. 2 is an explanatory view explaining a resistance measurement method by which the resistance of an unwanted radiation prevention member is measured, the member being provided in a gap between the housing section 30 and the door section 31 of the rack shown in FIG. 1. In part (a) of FIG. 2, a first step of the resistance measurement method is shown, and in part (b) of FIG. 2, a second step of the resistance measurement method is shown. As described above, various kinds of members for unwanted radiation prevention member may be conceivable including a conductive rubber and a conductive cloth. As an example of the unwanted radiation prevention member shown in FIG. 2, conductive cloths with an adhesive applied are used (hereinafter, simply referred to as conductive cloths), so that the conductive cloths are stuck to the rack.

FIG. 2 shows an example where, using a first embodiment of the present invention, the electric resistances of the conductive cloths manufactured by different manufacturers are respectively measured to evaluate the shielding performances of the respective conductive cloths.

First, referring to FIG. 2, examples of elements used for the first embodiment of the resistance measurement method of the present invention will be described.

For elements used for making a measurement using the resistance measurement method of the present invention, conductive cloths 2a, 2b . . . of companies A, B . . . are prepared as shown in FIG. 2. As an example of conductive plates making a pair of conductive plates, zinc galvanized steel plates (zinc electroplated steel plates) 1a and 1b are prepared in advance, and flexible conductive materials 10 to be held between the two zinc galvanized steel plates (zinc electroplated steel plates) 1a and 1b are also prepared in advance. The width and the length of this flexible conductive material 10 are smaller than those of each one of the conductive cloths 2a and 2b. A spacer 11 is also prepared, and the thickness of the spacer 11 is thinner than the flexible conductive material 10 in an uncompressed state. This spacer 11 is a rectangular frame with a hollow formed therein and made of an insulating material. Two pieces of the flexible conductive materials 10 are disposed on the both sides of the spacer 11. One of the conductive cloths 2a, 2b . . . of the companies A, B . . . is stuck to the inner surface of the zinc galvanized steel plate (zinc electroplated steel plates) 1b (i.e., a surface where the flexible conductive materials 10 are disposed) out of the pair of the zinc galvanized steel plates (zinc electroplated steel plates) 1a and 1b. Specifically, one of the conductive cloths 2a, 2b . . . is stuck to the inner surface of the zinc galvanized (electroplated) steel plate 1b such that the conductive cloth is located between the zinc galvanized (electroplated) steel plate 1b and the flexible conductive material 10. Subsequently, the flexible conductive materials 10 are held between the pair of zinc galvanized steel plates (zinc electroplated steel plates) 1a and 1b, and the flexible conductive materials 10 are compressed until the thicknesses of the flexible conductive materials 10 becomes equal to the thickness of the spacer 11. Thereafter, the electric resistance is measured.

The electric resistances of conductive cloths of the different companies are thus respectively measured one after another to evaluate the shielding performance of the conductive cloths of the companies.

The resistance measurement method will be described below.

As shown in part (a) of FIG. 2, in a first step, the flexible conductive materials 10 are held between the two zinc galvanized steel plates (zinc electroplated steel plates) 1a and 1b, and the spacer 11 is held between the two zinc galvanized steel plates (zinc electroplated steel plates) 1a and 1b to regulate the space therebetween, whereby between one of the two zinc galvanized steel plates (zinc electroplated steel plates) 1a and 1b, and the flexible conductive materials 10, conductive cloths (the conductive cloths 2a of the company A, for example) are held. Although the flexible conductive materials 10 are disposed on both sides of the frame-shaped spacer 11 shown in part (a) of FIG. 2, the sum of the sizes of the flexible conductive materials 10 and the spacer 11 is a size fit with the size of the zinc galvanized steel plates (zinc electroplated steel plates) 1a and 1b. Accordingly, the flexible conductive materials 10 can be held by the two zinc galvanized steel plates (zinc electroplated steel plates) 1a and 1b with the spacer 11. The size of the conductive cloths 2a is larger than that of one flexible conductive material 10. Thus, on the side of conductive materials 10 where the conductive cloths 2a are interposed between the zinc galvanized (electroplated) steel plate 1b and the flexible conductive materials 10, the zinc galvanized (electroplated) steel plate 1b is not in contact with the flexible conductive materials 10.

In the second step, as shown in part (b) of FIG. 2, pressures are applied to both the top surface of the zinc galvanized (electroplated) steel plate 1a and the undersurface of the zinc galvanized (electroplated) steel plate 1b, in order to make the heights of the flexible conductive materials 10 become the same height as the spacer 11. After the compression, a probe is brought into contact with each surface of the two zinc galvanized steel plates (zinc electroplated steel plates) 1a and 1b to measure the electric resistance.

When a measurement is made by using this resistance measurement method, a compression state of the flexible conductive materials 10 can be constantly maintained by maintaining a constant spacing between the two zinc galvanized steel plates (zinc electroplated steel plates) 1a and 1b using the spacer 11. Further, as described above, since the two zinc galvanized steel plates (zinc electroplated steel plates) 1a and 1b are pressurized from above and under surfaces thereof, the zinc galvanized (electroplated) steel plate 1a and the flexible conductive materials 10, and the flexible conductive materials 10 and the conductive cloth 2a are firmly in contact with each other due to the compression. Further, the conductive cloths 2a and the zinc galvanized (electroplated) steel plate 1b are firmly attached to each other by an adhesive. For this reason, displacement of the contact condition and a deformation of the conductive cloth 2a are less likely to occur. Consequently, electric resistance of all the cloths from the different companies can be respectively and accurately measured under the same measuring condition.

Figure 3:
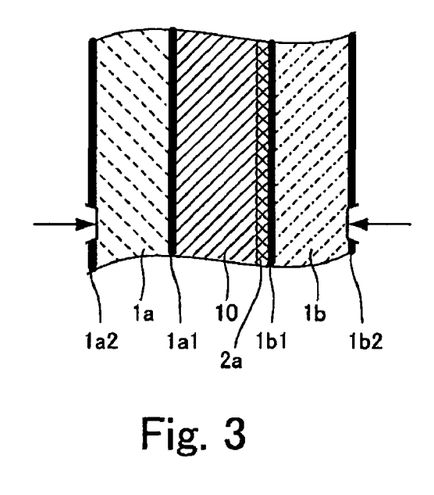
FIG. 3 is a sectional view showing a cutting plane formed by cutting a conductive cloth, a flexible conductive material, and two zinc galvanized (electroplated) steel plates shown in FIG. 2.

FIG. 3 is a sectional view showing a cutting plane formed by cutting the conductive cloth 2a, the flexible conductive material 10, and the two zinc galvanized steel plates (zinc electroplated steel plates) 1a and 1b shown in FIG. 2.

In the resistance measurement method of FIG. 2, to improve the measurement accuracy by considering that a surface treatment such as a corrosion protection film is performed by the manufacturers of the zinc galvanized steel plates (zinc electroplated steel plates) 1a and 1b, the surfaces of films 1a2 and 1b2 are scraped in order for the probes to come in contact, and then electric resistance, including those of films 1a1 and 1b1 formed on the surfaces of the zinc galvanized (electroplated) steel plates 1a an 1b respectively facing the flexible conductive material 10, is measured.

The films 1a2 and 1b2, formed on surfaces of which probes are brought into contact with the two zinc galvanized steel plates (zinc electroplated steel plates) 1a and 1b, are thus scraped, and the contact resistance of the probes is reduced. As a result, even though the electric resistance of the zinc galvanized steel plates (zinc electroplated steel plates) 1a and 1b is small, it is possible to accurately measure the electric resistances of the zinc galvanized steel plates (zinc electroplated steel plates) 1a and 1b, including films formed on the surfaces of the zinc galvanized (electroplated) steel plates 1a an 1b that face the flexible conductive materials 10 are disposed.

Here, an evaluation method of the resistance of the conductive cloth 2a will be described below with reference to FIG. 4.

Figure 4:
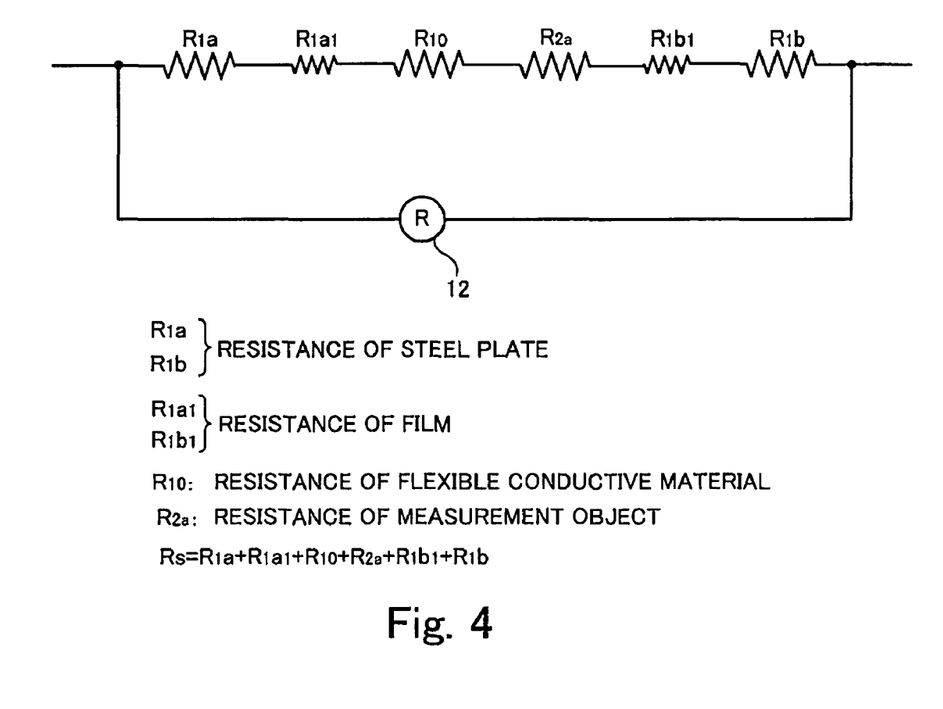
FIG. 4 is a view explaining resistance components of the object to be measured by the resistance measurement method explained in FIGS. 2 and 3.

FIG. 4 is a view explaining resistance components of the objects to be measured by the resistance measurement method explained in FIGS. 2 and 3. Incidentally, a resistance value R10 of the flexible conductive material 10 is assumed to be measured in advance, and therefore is a known value. Further, the steel plate portion of the zinc galvanized (electroplated) steel plate is metal, and thus, the resistance thereof is assumed to be approximately zero.

As shown in FIG. 3, one film is broken, and a probe is brought into contact with the broken portion to make a measurement. A series resister value Rs is measured by adding: a resistance value R1a of the zinc galvanized (electroplated) steel plate; a resistance value R1a1 of the film, of the zinc galvanized (electroplated) steel plate 1a, on the side on which the flexible conductive material 10 is disposed; a resistance value R10 of the flexible conductive material; a resistance value R2a of the conductive cloth which is the measurement object; a resistance value R1b1 of the film, of the other zinc galvanized (electroplated) steel plate 1b, on the side on which the flexible conductive material 10 is disposed; and a resistance value R1b of the zinc galvanized (electroplated) steel plate 1b. Further, as shown in FIG. 2, although the conductive cloths to be measured are disposed on two positions on the zinc galvanized (electroplated) steel plate, the resistance value R10 of the flexible conductive material, and the resistance value R2a of the conductive cloth are values corresponding to the entire area on such arrangement.

After measuring this series resistance value Rs, the resistance value R10 of the flexible conductive material is subtracted from the series resistance value Rs so that a resistance value including those of the conductive cloth 2a and the two zinc galvanized steel plates (zinc electroplated steel plates) 1a and 1b is calculated.

Even when the conductive cloths of different companies are used as measurement objects, the resistance values R1a1 and R1b1 of the films of the two zinc galvanized (electroplated) steel plates do not change. Thus, after the conductive cloths of the companies A, B . . . , are respectively measured and the respective resistance values of the cloths are calculated, and compared with each other. Thus, the shielding performances of the conductive cloths are evaluated. Here, after the resistance values of the different companies are compared one another and, for example, the electric resistance of the conductive cloths of the company B is determined to be the smallest, the conductive cloths of the company B are selected as an unwanted radiation prevention member to be provided in the gaps of cabinet and racks.

As described above, when the electric resistances are accurately measured for all the measurement objects under the same condition and compared with each other, favorable measurement results are obtained. Accordingly, accurate and fair evaluation is made. As described above, it is possible to achieve the resistance measurement method by which an accurate measurement of the electric resistance of cloth-like measurement objects can be made, for example.

Further, in the above embodiment, the zinc galvanized (electroplated) steel plates on the surfaces of which films are formed are used as an example of the conductive plates by which measurement objects and flexible conductive materials are held. However, the conductive plates of the present invention may be conductive plates on which films are not formed, or may be organic materials having electric conductivity.

Moreover, in the above embodiment, an insulating spacer is used as a desirable spacer, but the spacer of the present invention may be other than an insulating spacer as long as the spacer has a sufficiently high resistance value.

Here, note that when conductive cloths are manufactured by the manufacturer selected in the above embodiment and provided as a component, the provided conductive cloths do not necessarily have the same electric resistance as measured when the manufacturer is selected.

When the conductive cloths having the electric resistance measured when the manufacturer is selected are used for fabricating racks and cabinets, a predetermined shielding performance can be definitely obtained. However, conductive cloths manufactured by manufacturers are not uniform in quality; thus, all the conductive cloths do not have the same electric resistance.

Thus, it is desirable, at the time of receiving conductive cloths, to determine whether to receive the conductive cloths as the component by using the electric resistance measured when the manufacturer is selected as an inspection reference.

Figure 5:
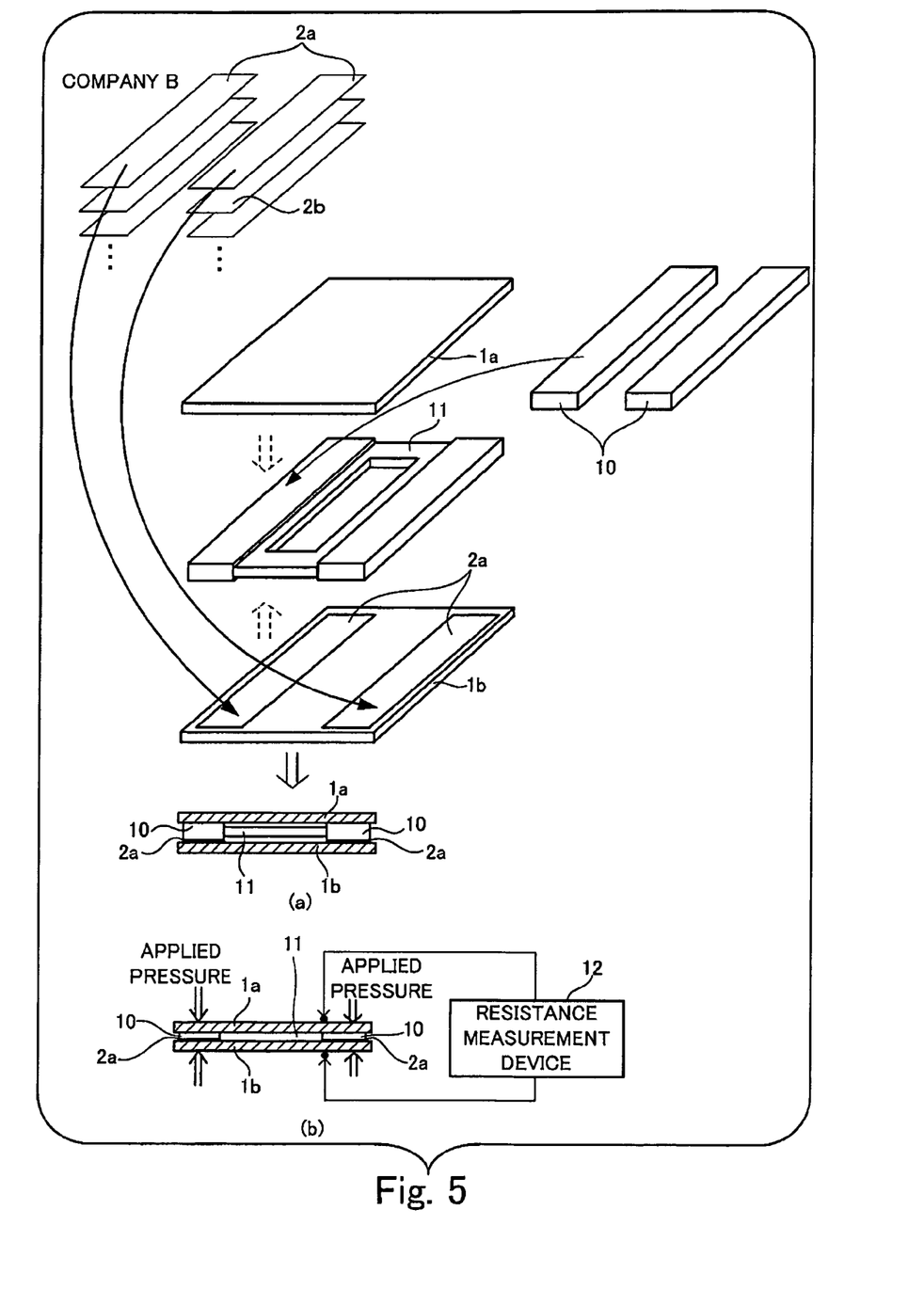
FIG. 5 is a view explaining an example where the resistance measurement method of the present invention is applied to a component inspection process.

FIG. 5 is a view explaining an example in the case where the resistance measurement method of the present invention is applied to a component inspection process. In FIG. 5, an example is shown in the case where the resistance measurement method of the first embodiment shown in FIG. 2 is applied to the component inspection process as it is.

Part (a) of FIG. 5 shows that there are a number of conductive cloths 2a, 2b . . . delivered from the company B which is the selected manufacturer. Conductive cloths to be measured are sampled from among a number of conductive cloths 2a, 2b . . . and measurements of the electric resistance of the conductive cloths are made one after another by the resistance measurement method described in FIG. 2. Subsequently, it is determined whether the measured electric resistance is not greater than the predetermined value.

Only when the electric resistance, measured by the resistance measurement method applied to the component inspection process shown in FIG. 5, is not greater than the predetermined value, the measured conductive cloths pass the receiving inspection. Thereafter, the conductive cloths are brought into the manufacturing site and used as the unwanted radiation prevention member to be provided in the gap of racks and cabinets.

As described above, by applying the resistance measurement method of the present invention to the component inspection process at the time of receiving the component, only measurement objects (here, conductive cloths), which have electric resistances to exert shielding performances, are sampled so that racks and cabinets having the predetermined shielding performances are fabricated.

Meanwhile, in the above embodiment, the description is given to the case where the flexible conductive material and the zinc galvanized (electroplated) steel plates are always the same ones, but resistance values of these conductive materials and zinc galvanized (electroplated) steel plates may possibly change with time. In particular, the anti-corrosion protection film or the like on the zinc galvanized (electroplated) steel plate is very likely to be worn down since a number of measurement objects are repeatedly stuck to and removed from the zinc galvanized (electroplated) steel plate one after another. However, if a zinc galvanized (electroplated) steel plate with no anti-corrosion protection film or the like formed thereon is used, a surface resistance is very likely to change due to rust or the like.

Therefore, it is desirable that a resistance value of other elements other than the measurement object be measured in the manner described below.

Figure 6:
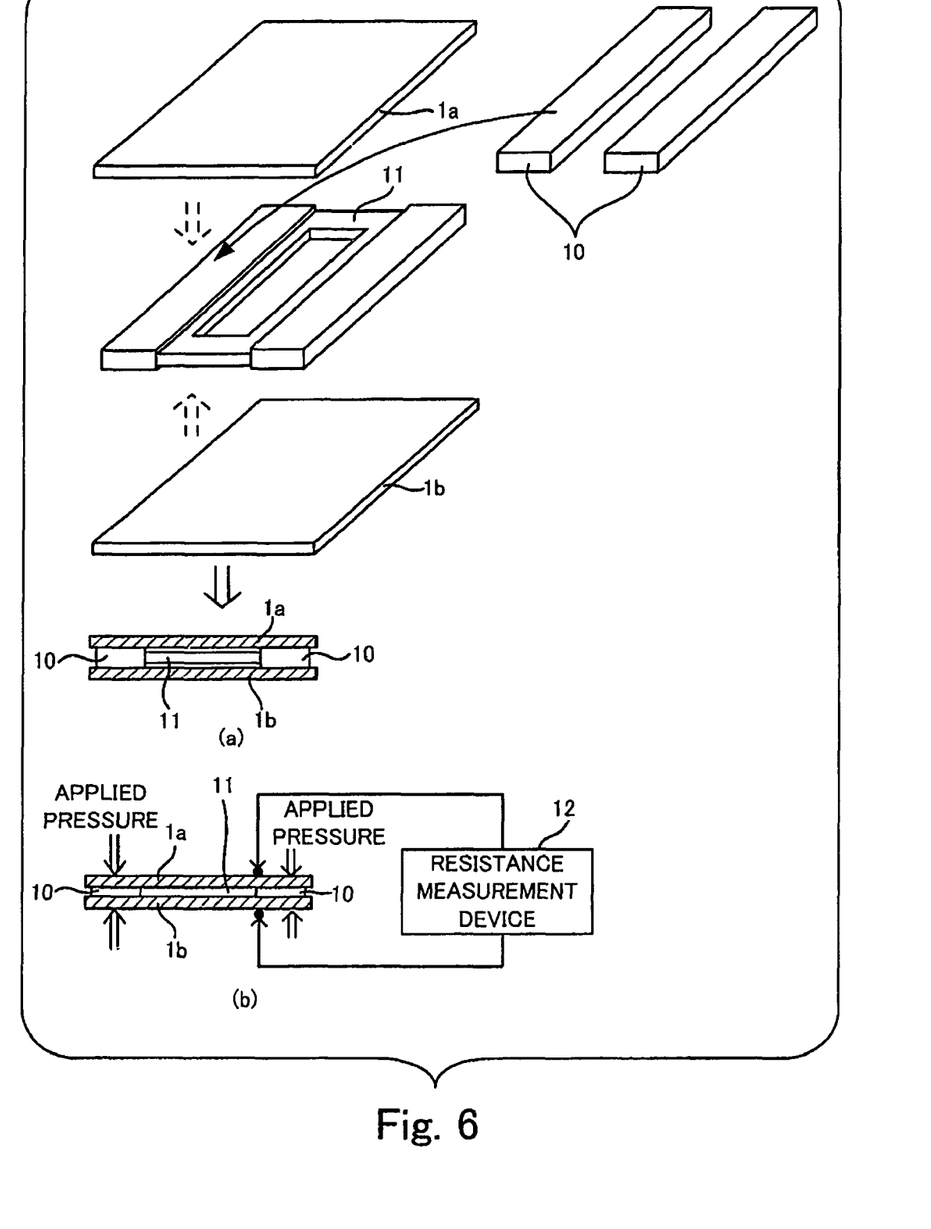
FIG. 6 is a view explaining a second embodiment of the present invention.

FIG. 6 is a view explaining a second embodiment of the present invention.

In this embodiment, the first step shown in part (a) of FIG. 2 and the second step shown in part (b) of FIG. 2 are also performed without change. Moreover, a third step shown in part (a) of FIG. 6 and a fourth step shown in part (b) of FIG. 6 are also performed.

In the third step shown in part (a) of FIG. 6, the two zinc galvanized steel plates (zinc electroplated steel plates) 1a and 1b, the flexible conductive materials 10, and the spacer 11 used in the first step of part (a) of FIG. 2 are also used without change. The flexible conductive materials 10 are held between the two zinc galvanized steel plates (zinc electroplated steel plates) 1a and 1b, and the spacer 11 is also held between the two zinc galvanized steel plates (zinc electroplated steel plates) 1a and 1b to regulate the space therebetween.

Further, in the fourth step of part (b) of FIG. 6, pressures are applied to the two zinc galvanized steel plates (zinc electroplated steel plates) 1a and 1b from both surfaces thereof to make the heights of the flexible conductive materials 10 become the same height as the spacer 11. After the compression, a probe is brought into contact with each one of the two zinc galvanized steel plates (zinc electroplated steel plates) 1a and 1b to measure the electric resistance.

Resistance values thus obtained by the measurement are subtracted from the resistance values obtained by the measurement shown in FIG. 2, whereby the resistance value of a measurement object alone can be accurately obtained. As a result, the selection of manufacturers and evaluation of components are improved in accuracy.

Further, the third step and the fourth step of parts (a) and (b) of FIG. 6 may be performed before or after performing the first and second steps. When an elapsed time in which the resistance value of a zinc galvanized (electroplated) steel plate changes is short enough to be neglected, the third step and the fourth step may be performed only one time after or before performing the first and second steps for multiple measurement objects.

Another embodiment in which the first step is different from that of the above embodiments will be described below.

Figure 7:
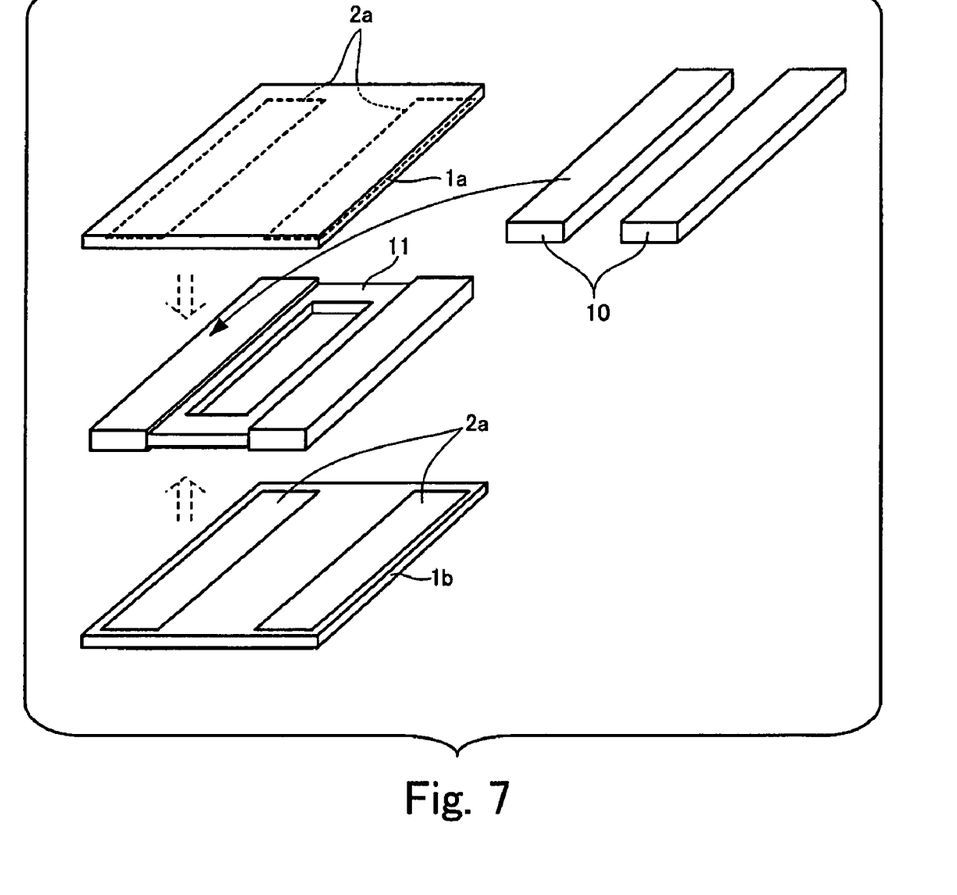
FIG. 7 is a view explaining a third embodiment of the present invention.

FIG. 7 is a view explaining a third embodiment of the present invention.

In the third embodiment, conductive cloths 2a to be measured are stuck to both of two zinc galvanized steel plates (zinc electroplated steel plates) 1a and 1b. As in the first embodiment, flexible conductive materials 10 are held between the two zinc galvanized steel plates (zinc electroplated steel plates) 1a and 1b, and a spacer 11 is also held between the two zinc galvanized steel plates (zinc electroplated steel plates) 1a and 1b to regulate the space therebetween. At this time, the conductive cloths 2a are interposed between the flexible conductive materials 10 and the zinc galvanized (electroplated) steel plate 1a, and on the side between the flexible conductive materials 10 and the zinc galvanized (electroplated) steel plate 1b. Accordingly, though in this third embodiment, a resistance value obtained by the measurement in the second step shown in part (b) of FIG. 2 includes the resistance values of two of the conductive cloths, an accurate and stable resistance value measurement is still achieved similarly to the first embodiment.

Figure 8:
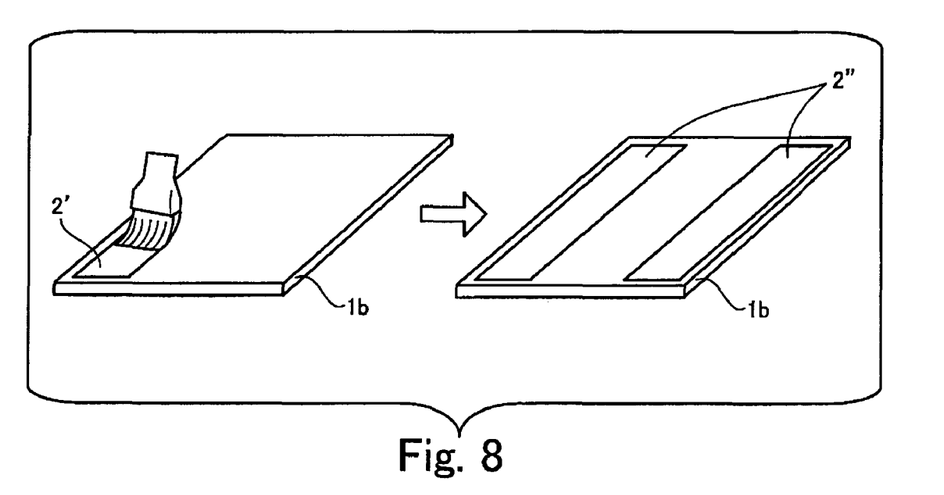
FIG. 8 is a view explaining a fourth embodiment of the present invention.

FIG. 8 is a view explaining a fourth embodiment of the present invention.

In the fourth embodiment, it is assumed that surfaces of plate materials received as raw materials for cabinets and racks are painted at a manufacturing site of racks and cabinets. Then, the resistances of films formed by the painting are measured. This embodiment is one which fulfills a desire to measure the resistance of the paint film alone independently of the plate materials to be painted and to evaluate only the paint film.

While the measurement objects are stuck to a zinc galvanized (electroplated) steel plate or both of the zinc galvanized (electroplated) steel plates in the above respective embodiments, paint 2' is applied using a brush or a spray to a zinc galvanized (electroplated) steel plate 1b in this fourth embodiment. By drying the paint 2', paint films 2" which are measurement objects are formed. The zinc galvanized (electroplated) steel plate 1b with the paint film 2" formed thereon is used to measure a resistance value in the same manner as that of each of the above embodiments. Consequently, the resistance value of the paint film 2" can be accurately and stably measured. Note that, in this embodiment, there may be a case where it is difficult to remove the paint film 2" without damaging the zinc galvanized (electroplated) steel plate 1b. Therefore, it is preferable to perform the third step and the fourth step shown in FIG. 6 before applying the paint 2' to the zinc galvanized (electroplated) steel plate 1b.

Figure 9:
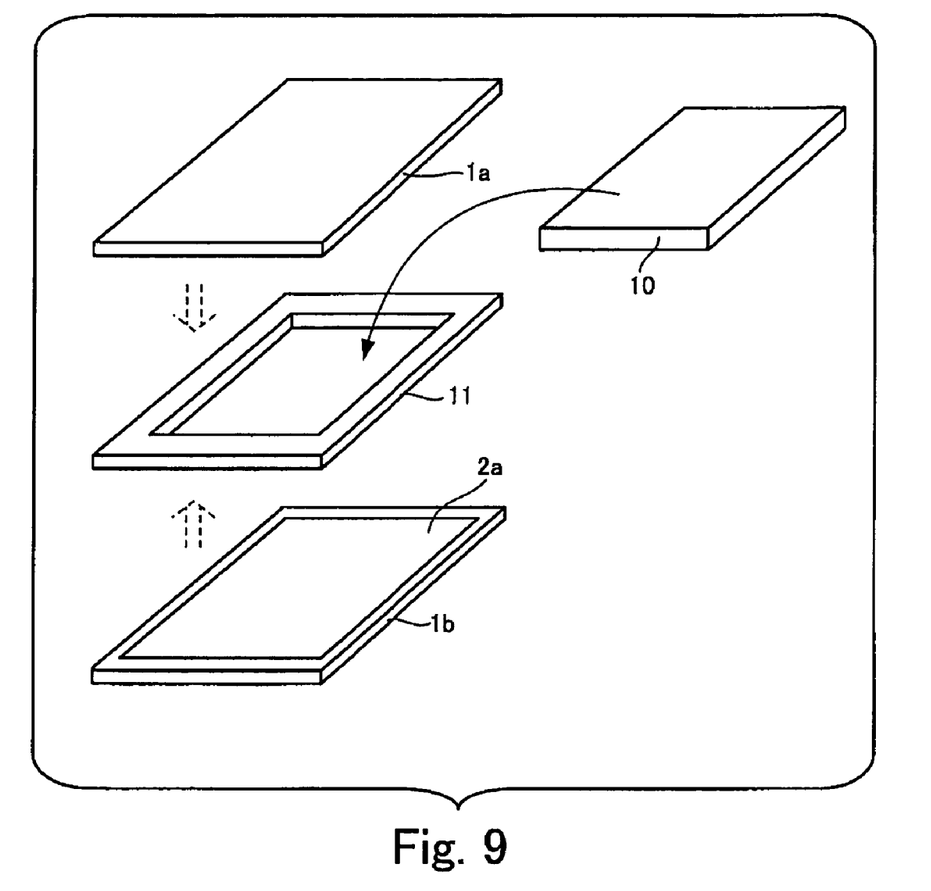
FIG. 9 is a view explaining a fifth of the present invention.

FIG. 9 is a view explaining a fifth embodiment of the present invention.

This fifth embodiment gives a description of the case where a measurement object having a sufficiently large area is obtained.

In the fifth embodiment, for a spacer 11, one having the same outer size as those of the zinc galvanized steel plates (zinc electroplated steel plates) 1a and 1b is used, and a flexible conductive material 10 is disposed inside the frame of this spacer 11. Moreover, a measurement object (a conductive cloth 2a in this example) with a size larger than that of the flexible conductive material 10 is prepared, and stuck to the zinc galvanized (electroplated) steel plate 1b. In addition, the flexible conductive material 10 and a spacer 11 are held between the two zinc galvanized steel plates (zinc electroplated steel plates) 1a and 1b, and the conductive cloth 2a is held between the flexible conductive material 10 and the zinc galvanized (electroplated) steel plate 1b.

In this fifth embodiment, the stability of a resistance value measurement is high because the area of the flexible conductive material 10 is large.

What is claimed is:

1. A resistance measurement method comprising:
   first processing including sandwiching a flexible conductive material by two conductive plates with a pressing force such that the two conductive plates approach each other, and interposing a measurement object between one of the two conductive plates and the flexible conductive material; and
   second processing including measuring electric resistance between the two conductive plates that sandwich the flexible conductive material therebetween with the measurement object interposed, wherein
   the first processing includes holding a spacer as well as the flexible conductive material between the two conductive plates, the spacer regulating a space between the two conductive plates, and
   the spacer is thinner than the flexible conductive material which is in an uncompressed state.

2. The resistance measurement method according to claim 1, further comprising:
   third processing including sandwiching the flexible conductive material by the two conductive plates with a pressing force such that the two conductive plates approach each other in the same state as the first processing but without interposing the measurement object between the two conductive plates; and
   fourth processing including measuring electric resistance between the two conductive plates that sandwich the flexible conductive material therebetween without interposing the measurement object, wherein
   the third processing and fourth processing are performed before or after the first processing and second processing.

3. The resistance measurement method according to claim 1, wherein the electric resistance value of the flexible conductive material is known.

4. The resistance measurement method according to claim 1, wherein the conductive plate is made of any one of a zinc galvanized steel plate, a zinc electroplated steel, a stainless steel plate, a steel plate, a copper plate, an alloy material, aluminum and a resin.

5. The resistance measurement method according to claim 1, wherein the spacer is an insulating material.

6. A component inspection process of measuring the electric resistance of an inspection object to determine whether the inspected object is acceptable according to the measurement result, the process comprising:
   first processing including sandwiching a flexible conductive material by two conductive plates with a pressing force such that the two conductive plates approach each other, and interposing a measurement object between one of the two conductive plates and the flexible conductive material; and
   second processing including measuring electric resistance between the two conductive plates that sandwich the flexible conductive material therebetween with the measurement object interposed, wherein
   the first processing includes holding a spacer as well as the flexible conductive material between the two conductive plates, the spacer regulating a space between the two conductive plates, and
   the spacer is thinner than the flexible conductive material which is in an uncompressed state.

* * * * *